United States Patent [19]
Petrosky

[11] Patent Number: 5,426,256
[45] Date of Patent: Jun. 20, 1995

[54] MINIMIZING HEAVY ENDS PRODUCTION IN THE MANUFACTURE OF PERCHLOROETHYLENE FROM HYDROCARBONS OR PARTIALLY CHLORINATED HYDROCARBONS

[75] Inventor: Jimmie T. Petrosky, Wichita, Kans.

[73] Assignee: Vulcan Materials Company, Wichita, Kans.

[21] Appl. No.: 252,400

[22] Filed: Jun. 1, 1994

Related U.S. Application Data

[63] Continuation of Ser. No. 16,237, Feb. 11, 1993, abandoned.

[51] Int. Cl.$^6$ .................. C07C 17/02; C07C 17/013; C07C 17/04
[52] U.S. Cl. ..................................... 570/234; 570/237; 570/218
[58] Field of Search ........................ 570/234, 237, 218

[56] References Cited

U.S. PATENT DOCUMENTS

| | | | |
|---|---|---|---|
| 1,930,350 | 10/1933 | Strosacker et al. | 260/166 |
| 2,442,323 | 5/1948 | Davis et al. | 260/654 |
| 2,442,324 | 5/1948 | Heitz et al. | 260/654 |
| 2,447,410 | 8/1948 | Hampel | 260/654 |
| 2,577,388 | 12/1951 | Warren | 260/654 |
| 2,727,076 | 12/1955 | Warren | 260/658 |
| 2,857,438 | 10/1958 | Obrecht et al. | 260/654 |
| 3,234,295 | 2/1966 | Sprauer | 570/218 |
| 3,364,272 | 1/1968 | Ager, Jr. | 260/654 |
| 4,002,695 | 1/1977 | Gorton et al. | 260/654 D |
| 5,023,387 | 6/1991 | West et al. | 570/252 |

*Primary Examiner*—Howard T. Mars
*Attorney, Agent, or Firm*—Burns, Doane, Swecker & Mathis

[57] ABSTRACT

Perchloroethylene and hydrogen chloride are made by thermal noncatalytic chlorination of hydrocarbons and/or their partially chlorinated derivatives using carbon tetrachloride as a reactive diluent under conditions which maximize consumption of carbon tetrachloride and minimize the production of heavy ends, such as hexachlorobenzene and other tarry products.

21 Claims, 2 Drawing Sheets

MINIMIZING HEAVY ENDS PRODUCTION IN THE MANUFACTURE OF PERCHLOROETHYLENE FROM HYDROCARBONS OR PARTIALLY CHLORINATED HYDROCARBONS

This application is a continuation of application Ser. No. 08/016,237, filed Feb. 11, 1993, now abandoned.

BACKGROUND OF THE INVENTION

1. Field of the Invention

This invention relates to a process for making perchloroethylene and hydrogen chloride by thermal noncatalytic chlorination of hydrocarbons and/or their partially chlorinated derivatives in the presence of carbon tetrachloride. In particular, it relates to a process for the production of perchloroethylene using carbon tetrachloride as a reactive diluent under conditions which maximize consumption of unwanted carbon tetrachloride while minimizing the production of heavy ends, such as hexachlorobenzene and other tarry products.

2. Background of the Invention

When perchloroethylene is manufactured by a conventional process involving chlorination of hydrocarbons and/or their partially chlorinated derivatives, substantial amounts of carbon tetrachloride are also obtained. In addition, substantial quantities of undesirable highly chlorinated products, hereinafter referred to as heavy ends, are formed such as hexachloroethane, hexachlorobutadiene and hexachlorobenzene. Carbon tetrachloride is thought to be among the halocarbons which cause destruction of the ozone layer and it has also been used as a feedstock in producing environmentally deleterious halogenated chlorofluorocarbons. Because of the undesirable environmental effects of carbon tetrachloride, regulations governing the production and use of carbon tetrachloride are expected to result in a marked decrease in carbon tetrachloride production over the next decade. The heavy ends resulting from conventional chlorination processes are also undesirable and their disposal by burning can result in emission of undesirable compounds into the atmosphere. On the other hand, the more benign chlorinated hydrocarbons, notably perchloroethylene, will likely remain in demand because of their many practical uses. Perchloroethylene especially, because it is ecologically acceptable, is in high demand both as a solvent and as a starting material for the production of other chemicals. The present invention addresses these problems by providing a process that consumes carbon tetrachloride and minimizes formation of heavy ends in the production of perchloroethylene.

Direct thermal chlorination of methane, ethane, propane, ethylene, propylene, or their partially chlorinated derivatives exemplifies a conventional process for perchloroethylene production. The chemical reactions for the chlorination of these hydrocarbons and/or their partially chlorinated derivatives are exothermic. They can therefore result in carbon formation or result in an explosion from a runaway reaction if the temperature of the reaction is not controlled. One method of controlling the temperature in the reaction zone is to add a coolant or diluent to the feed mixture. A diluent is defined as any material that is injected into the reactor in order to moderate or control the reactor temperature. The use of vaporized carbon tetrachloride as a diluent to control reactor temperature is disclosed, for example in U.S. Pat. Nos. 2,577,388 and No. 2,442,323. These patents also disclose recycling of reaction products and use of other variables to control the ratio of carbon tetrachloride to perchloroethylene in the product stream. Use of a liquid diluent made up of chlorinated aliphatic compound such as carbon tetrachloride, perchloroethylene, hexachloroethane, hexachlorobutadiene, and mixtures thereof, is disclosed in U.S. Pat. No. 2,857,438.

SUMMARY OF THE INVENTION

Figure 1:
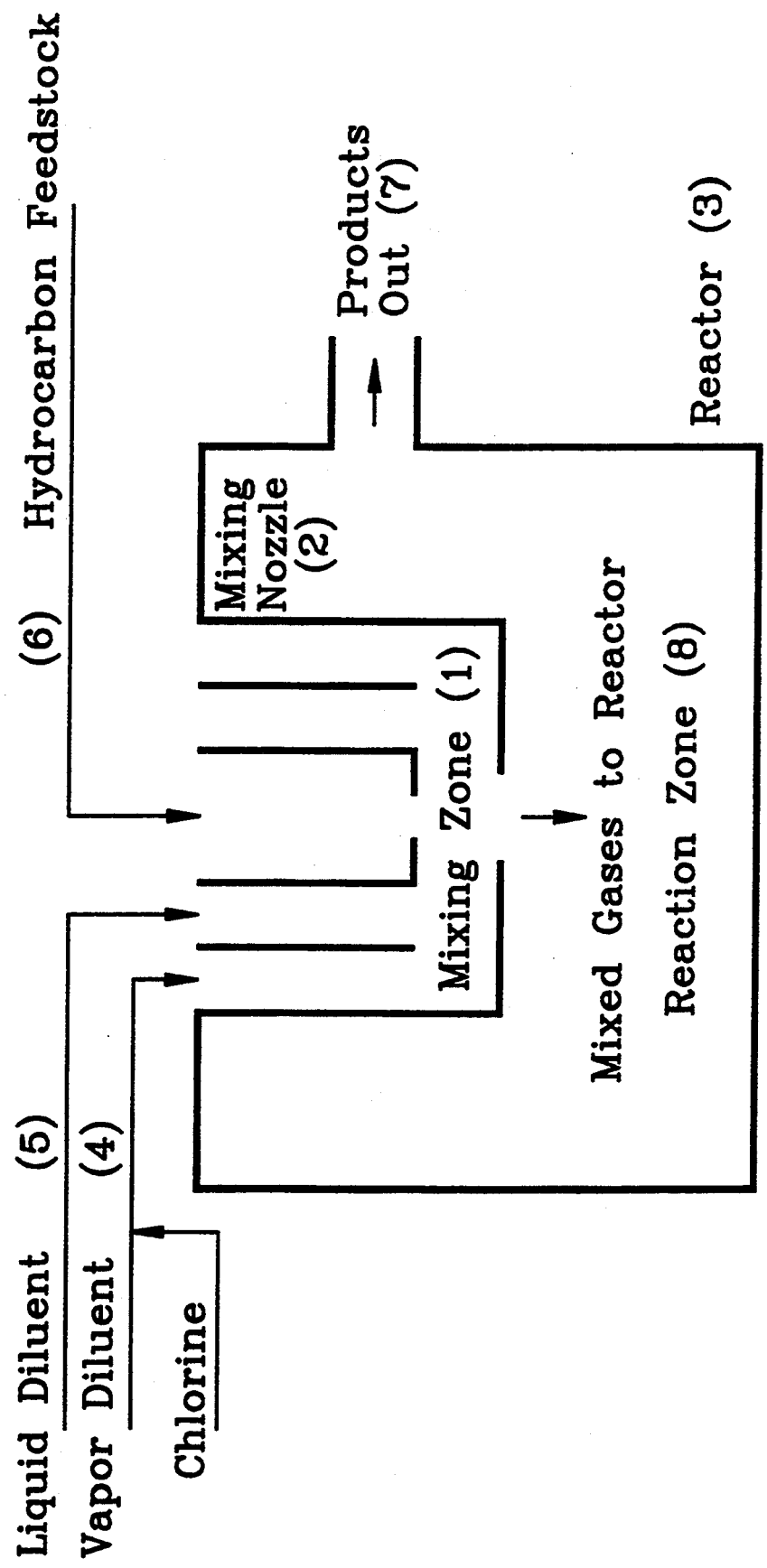
FIGS. 1 and 2 are schematic representations of two types of mixing diagrams for introducing feed into the reaction zone. The feed is introduced into a mixing nozzle with a mixing zone where the reactants are pre-mixed. The mixing nozzle is inserted into a feed port into the reaction zone of the reactor. The feed comprising the pre-mixed reactants is discharged from the mixing nozzle into the reaction zone of the reactor.

The present invention provides a process for making perchloroethylene by thermal noncatalytic chlorination of a hydrocarbon feedstock, partially chlorinated hydrocarbon feedstock, or mixture thereof, comprising a compound of the formula $C_xH_yCl_z$, wherein $x=1$ to 3, $y=1$ to 8 and $z=0$ to 6, provided that $y+z$ equals $2x+2$ when the compound is saturated and equals $2x$ when the compound contains a double bond, as exemplified, for instance, by methane, ethane, propane, ethylene, propylene, and their partially chlorinated derivatives, which comprise introducing the hydrocarbon feedstock, partially chlorinated hydrocarbon feedstock, or mixture thereof, and chlorine into a mixing nozzle inserted into a reactor with a reaction zone maintained at a temperature in the range between about 500° C. and about 700° C. The chlorine can be introduced in an amount sufficient to react with the hydrocarbon and/or partially chlorinated hydrocarbon feedstock and result in unreacted chlorine in the reactor effluent. Chlorine is preferably introduced in an amount sufficient to result in between about 3 and about 15 volume percent of free chlorine in the reactor effluent or product mixture. Carbon tetrachloride is introduced as a diluent into the feed port or inlet of a mixing zone of a mixing nozzle inserted into the reaction zone. The diluent is between about 30% and about 85% vapor carbon tetrachloride and between about 70% and about 15% liquid carbon tetrachloride preferably, between about 50 and about 85% by weight vapor and between 50 and about 15% by weight liquid carbon tetrachloride. The amount of carbon tetrachloride in the reaction zone is sufficient to maintain the reaction temperature between about 500° C. and about 700° C.

A gaseous product mixture is withdrawn from the reaction zone, is condensed and is purified to separate a perchloroethylene fraction and a carbon tetrachloride fraction. Carbon tetrachloride separated from the product stream may be recycled to the reaction chamber to provide the required diluent and/or carbon tetrachloride from an extraneous source may be used. The process provides a net consumption of carbon tetrachloride and minimizes formation of heavy ends, such as hexachloroethane, hexachlorobutadiene and hexachlorobenzene.

DESCRIPTION OF THE PREFERRED EMBODIMENT OF THE INVENTION

The conversion of carbon tetrachloride to perchloroethylene is represented by the following equation:

$$2CCl_4 \underset{\text{Heat}}{\overset{\text{Heat}}{\rightleftarrows}} C_2Cl_4 + 2Cl_2 \qquad (1)$$

The reaction is an equilibrium reaction that is endothermic and favors the formation of carbon tenchloride under conditions normally found in the reactor. As previously stated, the promotion of the formation of perchloroethylene, a commercially important product, accompanied by maximum consumption of unwanted carbon tetrachloride is increasingly recognized as being desirable.

The present invention is directed to the use of a mixture of vaporized and liquid carbon tetrachloride as a diluent while controlling the reaction temperature between about 500° C. and about 700° C., preferably between about 575° C. and about 675° C., to improve the product selectivity by maximizing perchloroethylene production while unexpectedly decreasing heavy ends formation. By using a mixture of liquid and vapor carbon tetrachloride diluent, the diluent itself is consumed, product selectivity is improved and, unexpectedly, heavy ends formation is decreased.

The present invention relates to a process for making perchloroethylene by thermal noncatalytic chlorination of a hydrocarbon feedstock, partially chlorinated hydrocarbon feedstock, or mixture thereof. The "hydrocarbon feedstock," as this term is used in this specification, comprises a compound of the formula $C_xH_yCl_z$, wherein $x=1$ to 3, $y=1$ to 8 and $z=0$ to 6, provided that $y+z$ equals $2x+2$ when the compound is saturated and equals $2x$ when the compound contains one double bond, as exemplified, for instance, by methane, ethane, propane, ethylene, propylene, and their partially chlorinated derivatives, such as chloroform, methyl chloride, ethyl chloride, ethylene dichloride, trichloroethane, trichloropropane, and the like. With respect to methane, ethane and propane the results of total chlorination of the hydrocarbon are represented by the following equations:

$$CH_4 + 3Cl_2 \rightarrow 0.5\ C_2Cl_4 + 4HCl \qquad (2)$$

$$CH_4 + 4Cl_2 \rightarrow CCl_4 + 4\ HCl \qquad (3)$$

$$C_2H_6 + 5\ Cl_2 \rightarrow C_2Cl_4 + 6HCl \qquad (4)$$

$$C_2H_6 + 7\ Cl_2 \rightarrow 2CCl_4 + 6HCl \qquad (5)$$

$$C_3H_8 + 7 + Cl_2 \rightarrow 1.5 C_2Cl_4 + 8HCl \qquad (6)$$

$$C_3H_8 + 10Cl_2 \rightarrow 3CCl_4 + 8HCl \qquad (7)$$

Similar equations can be given for the total chlorination of the partially chlorinated derivatives of the hydrocarbons.

As stated earlier herein, the carbon tenchloride is introduced into the reaction zone to serve as a diluent in an amount sufficient to maintain the temperature between about 500° and about 700° C., preferably between about 575° and about 625° C. Temperatures below about 500° C. result in incomplete reaction of the hydrocarbon feedstock, lower conversions of carbon tetrachloride to perchloroethylene, and formation of partially chlorinated compounds, such as chloroform or trichloroethylene. Higher temperatures, above about 700° C., result in carbon formation. If desired, inert diluents such as hydrogen chloride and/or nitrogen may be used to help control reactor temperatures. However, it is preferred to recycle liquid and vapor carbon tetrachloride and perchloroethylene mixtures from the process separation and/or distillation steps as well as introduce extraneous carbon tetrachloride diluent in order to control reactor temperatures. The carbon tetrachloride is recycled and converted to perchloroethylene, resulting in carbon tetrachloride consumption. Perchloroethylene is recycled if distillation results in incomplete separation of perchloroethylene and carbon tetrachloride.

The ratio of carbon tetrachloride to hydrocarbon feedstock introduced into the reaction zone will depend upon the particular hydrocarbon feedstock, the amount of chlorine introduced, and the reactor conditions. In general, the ratio will be greater than about 1, preferably between about 1.5 and about 25.0. The particular ratio will depend upon the identity of the hydrocarbon feedstock. For example, for ethylene dichloride, the preferred ratio is between 1.5 and 2.5; for propane, the preferred ratio is between 20 and 25.

The carbon tetrachloride may be introduced into the reaction zone either as a pure compound or as part of a mixed stream containing other chlorinated hydrocarbons, such as chloroform, perchloroethylene, trichloroethylene, hexachlorobutadiene, hexachlorobenzene or hexachloroethane. However, it is preferred to use a chloro-organic stream which has a carbon tetrachloride concentration of at least 50 weight percent.

The chlorine, as previously stated, is introduced into the reaction zone in an amount sufficient to provide unreacted chlorine in the reactor effluent. The chlorine is introduced as elemental chlorine and as a product of the pyrolysis of carbon tetrachloride as shown in reaction (1). Preferably, chlorine will be introduced in an amount sufficient to result in between about 3% and about 15%, preferably between about 5% and about 7%, by volume of free, i.e., unreacted, chlorine in the reactor effluent or product mixture, which is commonly described as excess chlorine. Benefits of excess chlorine being introduced into the reaction zone, as stated in U.S. Pat. Nos. 2,442,324 and 2,727,076, include a reduction in the formation of heavy ends and the total chlorination of the hydrocarbon feedstock. Thus, by operating the reactor with an excess of chlorine in the reaction zone, the need for separating undesirable underchlorinated compounds in the purification step is eliminated.

Figure 2:
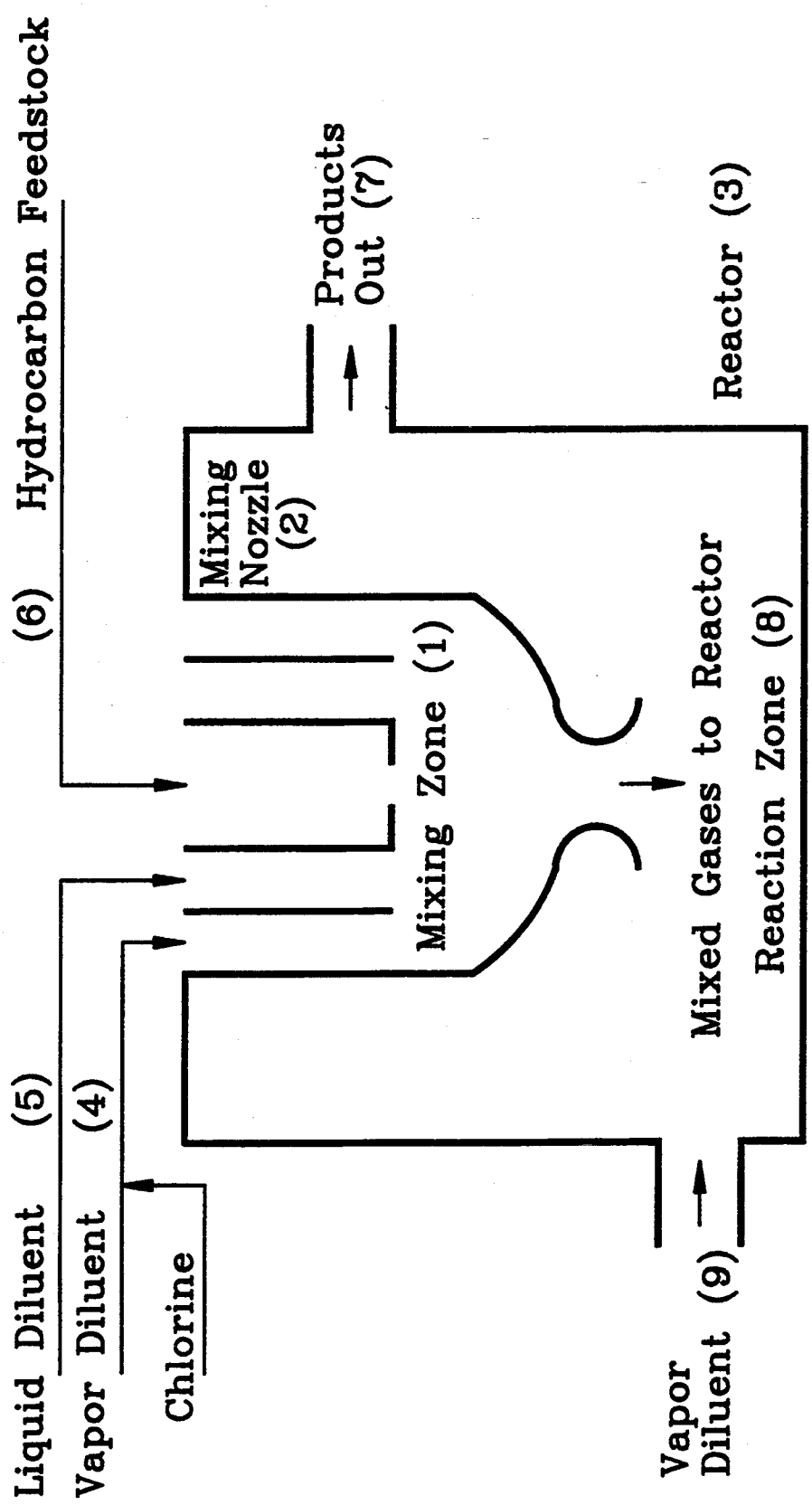

The reactants comprising the hydrocarbon feedstock, liquid and vapor carbon tetrachloride diluent, and chlorine are first introduced into an inlet of a mixing nozzle which is inserted or discharges into the reaction zone to achieve pre-mixing of the feed material. This practice improves the mixing efficiency of the reactants and thus increases the ability of the reaction zone to produce the desired products. Two types of mixing diagrams for introducing feed into the reaction zone of the reactor through a mixing nozzle are represented in FIGS. 1 and 2. The diagrams are meant only to be illustrative of the concept and should not be construed as all inclusive, thus limiting the invention.

As shown in FIG. 1, in the preferred method of feeding the vapor carbon tetrachloride diluent and chlorine can be introduced into the mixing zone (1) of the mixing nozzle (2) inserted into the reactor (3) through the same inlet of the mixing zone (4). The liquid diluent and the hydrocarbon feedstock can be inserted into separate inlets, for example (5) and (6). The reactor feed material enters the mixing zone (1) of the mixing nozzle (2) to pre-mix the reactants. The reactor feed material enters the mixing zone (1) and is inserted or discharges into the reaction zone (8) of the reactor (3). The products of the reaction are then discharged from the reactor (7).

As shown in FIG. 2, at least a portion of the vapor carbon tetrachloride diluent may be fed into the reactor in a feed port (9) separate from the mixing nozzle through which the hydrocarbon feedstock, chlorine, vapor and liquid carbon tetrachloride diluent are fed. Similarly, the chlorine could be fed separately directly into the reactor, however, there is no advantage to this method of feeding.

While the process of the present invention has been described as being conducted in one reactor, the present invention alternatively can be carried out in two separate reactor stages operating in series. The first stage consists of reacting the hydrocarbon feedstock with chlorine in the presence of carbon tetrachloride diluent. The reactor effluent is fed to a second stage reactor wherein additional chlorine and carbon tetrachloride diluent are injected.

Various factors are important in controlling the degree of mixing of the liquid phase reactor feed material and the vapor phase reactor feed material. These factors include the manner in which the liquid feed is introduced into the reaction zone of the reactor, the temperature and pressure of the liquid feed that is injected, the identity or composition of the liquid feed, the velocities of the materials to be mixed, and the conditions inside the reaction zone itself. In a preferred embodiment, the vapor feeds are introduced into the reaction zone of the reactor with a velocity through the orifice in the nozzle of at least about 30 meters per second (100 feet per second) and preferably between about 60 and about 77 meters per second (200 and about 250 feet per second). The upper limit on the velocity is sonic velocity, although such high velocity is not preferred. Although not essential to the invention, it may be desirable to heat the liquid and/or vapor feeds prior to injecting them into the reactor in order to increase the turbulence in the mixing zone of the mixing nozzle. Heating the vapor feed to a higher temperature increases the volumetric flow of the gas, which increases the velocity at which the vapor feed is introduced into the reaction zone and results in better mixing of the gases. Heating the liquid feed to a higher temperature increases its viscosity, which makes the liquid easier to atomize and results in better dispersion of the liquid in the vapor feed. One skilled in the art of nozzle design will recognize that additional methods may be useful in obtaining a high degree of turbulence in the mixing zone to promote good mixing prior to entering the reaction zone.

Reactor pressure is important, but not critical. While the preferred operating pressure is between about 0 and about 4.5 atmospheres gauge (50 psig), higher pressures can be employed. The reactor can either be a back-mixed or plug flow type with suitable refractory lining as is common in the industry.

The perchloroethylene product may be purified by conventional methods illustrated in the prior art, such as effluent quenching, condensing, and distillation in order to separate the perchloroethylene product from the carbon tetrachloride, HCl, chlorine and other by-products.

The invention may be understood in more detail from the following illustrative examples. It should be understood that these examples are not construed as limiting the invention.

EXAMPLE 1

Liquid 1,2-dichloroethane (EDC), vaporized chlorine, and a mixture of vapor and liquid diluent carbon tenchloride were continuously introduced into a back-mixed reactor chamber. The reactor chamber consisted of a carbon lined vessel consisting of about 1.9 cubic feet of volume. The reaction chamber was maintained at a temperature of approximately 595° C. and a pressure of approximately 3.7 atmospheres gauge (40 psig). The hot reaction gases at the exit of the reactor were indirectly cooled with water in a quench tower with a bottoms temperature of about 165° C. The vapors of carbon tetrachloride and perchloroethylene going overhead of the quench tower were condensed by indirect cooling to separate them from the hydrogen chloride and unreacted chlorine, and fractionally distilled to recover the product and carbon tetrachloride. In various test runs, some or all of the carbon tetrachloride was fed as liquid and some or all of the carbon tetrachloride obtained was vaporized in a heat exchanger and fed as a vapor back to the reactor.

The effect of varying the ratio of liquid to vapor carbon tenchloride diluent on perchloroethylene and heavy ends yields is shown in Table I. At constant feed rate of 1,2-dichloroethane and chlorine, various proportions of diluent carbon tetrachloride were vaporized from 0% to 100%. As seen in Table I, the ratio of perchloroethylene to heavy ends produced is maximized by the use of a mixed vapor and liquid diluent. The optimum minimization of heavy ends production appears to be using between about a 70/30 and a 75/25 split, by weight, between vapor and liquid diluent.

TABLE I

| | Test No. | | | | | |
|---|---|---|---|---|---|---|
| | 1 | 2 | 3 | 4 | 5 | 6 |
| Feeds, lb/hr | | | | | | |
| $Cl_2$ | 50 | 50 | 50 | 50 | 50 | 46.5 |
| EDC | 20 | 20 | 20 | 20 | 20 | 20.0 |
| Vapor $CCl_4$ | — | 21 | 29 | 29 | 40 | 47.5 |
| Liquid $CCl_4$ | 22 | 15 | 12 | 9 | 5 | — |
| Total | 92 | 106 | 111 | 108 | 115 | 114.0 |
| Vaporized Diluent, % by weight | 0 | 58.0 | 70.7 | 76.0 | 88.9 | 100 |
| Excess $Cl_2$ (in reactor effluent) | 6.7 | 6.1 | 6.9 | 6.5 | 6.8 | 5.6 |
| Products, lb/hr | | | | | | |
| $C_2Cl_4$ | 26.77 | 26.97 | 29.15 | 34.04 | 30.08 | 30.45 |
| Heavy Ends | 3.48 | 3.85 | 3.58 | 4.07 | 4.54 | 4.63 |
| Wt. Ratio of Products $C_2Cl_4$/Heavy Ends | 7.69 | 7.01 | 8.14 | 8.36 | 6.63 | 6.58 |

EXAMPLE 2

Example 1 is repeated with the exception that propane is used as the primary hydrocarbon feed instead of EDC. The effect of varying the ratio of liquid and vapor carbon tetrachloride diluent on perchloroethylene yield (production split and heavy ends formation) is shown in Table II. The production of perchloroethylene is maximized and the formation of heavy ends is minimized in this case when between about 55 and 65%, by weight, of the total diluent is fed as a vapor.

TABLE II

| | Test No. | | | |
|---|---|---|---|---|
| | 10 | 11 | 12 | 13 |
| Feeds, lb/hr | | | | |
| $Cl_2$ | 47.9 | 50 | 50 | 50 |
| Propane | 3.9 | 3.9 | 3.9 | 3.9 |
| Vapor $CCl_4$ | — | 38.9 | 54.8 | 65.0 |
| Liquid $CCl_4$ | 60.5 | 40.1 | 32.5 | 25.2 |
| Total | 114.1 | 132.9 | 141.2 | 144.1 |
| Vaporized Diluent, % by weight | 0 | 49.2 | 62.8 | 72.1 |
| Excess $Cl_2$ (in reactor effluent) | 6.5 | 5.4 | 5.3 | 6.9 |
| Products, lb/hr | | | | |
| $C_2Cl_4$ | 21.07 | 17.12 | 25.09 | 24.43 |
| Heavy Ends | 1.01 | .72 | .93 | 1.46 |
| Wt. Ratio of Products $C_2Cl_4$/Heavy Ends | 20.86 | 23.78 | 26.98 | 16.73 |

As can be seen from the examples, the chlorination of hydrocarbon or partially chlorinated hydrocarbon feedstock to produce perchloroethylene and consume carbon tetrachloride is maximized by the introduction of a mixture of vapor and liquid diluent into the reaction zone, while minimizing the production of unwanted heavy ends. The mixture of vapor and liquid carbon tetrachloride is preferably introduced into the reaction zone with between about 50 and about 85 percent of the carbon tetrachloride in the vapor form.

With the present teaching in hand, persons skilled in the art should be able to determine the optimum vapor/liquid diluent split by performing routine tests for each case. The particular ratio, however, will depend upon, for example, the particular hydrocarbon or partially chlorinated hydrocarbon feedstock, the reactor conditions and the amount of chlorine introduced.

While the invention has been described in terms of certain preferred embodiments, modifications obvious to one with ordinary skill in the art may be made without departing from the scope of the present invention.

What is claimed is:

1. A process for making perchloroethylene by thermal noncatalytic chlorination of a hydrocarbon feedstock, partially chlorinated hydrocarbon feedstock or mixture thereof, under conditions which maximize consumption of carbon tetrachloride, which process comprises:

introducing the following materials into a mixing zone:

(a) said hydrocarbon feedstock or partially chlorinated hydrocarbon feedstock comprising a compound of the formula $C_xH_yCl_z$, wherein x=1 to 3, y=1 to 8 and z=0 to 6, provided that y+z equals 2x+2 when the compound is saturated and equals 2x when the compound contains a double bond;

(b) chlorine, wherein said chlorine is introduced in an amount sufficient to convert the feedstock to perchloroethylene and result in free chlorine in the product mixture; and (c) carbon tetrachloride as a reactive diluent, said carbon tetrachloride introduced being between about 50 and about 85 percent by weight vapor and between about 50 and about 15 percent by weight liquid and wherein the amount of carbon tetrachloride so introduced is sufficient to maintain the temperature in the range of between about 500° and about 700° C;

discharging the resulting mixture from said mixing zone into a reaction zone wherein the temperature of the mixture is maintained within said temperature range and wherein carbon tetrachloride consumed and perchloroethylene is produced;

withdrawing a product mixture from the reaction zone;

condensing said mixture; and separating a perchloroethylene fraction and a carbon tetrachloride fraction therefrom.

2. The process of claim 1, wherein said feedstock is selected from the group consisting of ethylene dichloride, propane and mixture thereof, and wherein said chlorine is introduced in an amount sufficient to leave between about 3 and about 15 volume percent free chlorine in the product mixture.

3. The process of claim 1, wherein the ratio of said carbon tetrachloride to said feedstock introduced into said mixing zone is greater than one.

4. The process of claim 3, wherein the ratio of carbon tetrachloride to hydrocarbon feedstock introduced into said mixing zone is between about 1.5 and about 25.0.

5. The process of claim 1, wherein said chlorine is introduced in an amount sufficient to leave between about 3.0 and about 15 volume percent of free chlorine in the product mixture.

6. The process of claim 5, wherein said chlorine is introduced in an amount sufficient to leave between about 5 and about 7 volume percent of free chlorine in the product mixture.

7. The process of claim 1, wherein said separated carbon tetrachloride fraction is recycled to the reaction zone.

8. The process of claim 1, wherein said carbon tetrachloride is introduced into the reaction zone from an extraneous source.

9. The process of claim 1, wherein said feedstock, chlorine and carbon tetrachloride are introduced into the reaction zone by means of a mixing nozzle.

10. The process of claim 9, wherein the vapor carbon tetrachloride is fed into the reaction zone through a feed port that is separate from the feed port of the mixing nozzle through which the liquid carbon tetrachloride, hydrocarbon feed, and chlorine are fed.

11. The process of claim 1, wherein the temperature in the reaction zone is between about 575° and about 625° C. and the pressure in the reaction zone is between about 0 and about 10 atmospheres gauge.

12. The process of claim 11, wherein the pressure in the reaction zone is between about 1.0 and about 4.5 atmospheres.

13. The process of claim 1, wherein said reaction zone is in a back-mixed reactor or a plug flow type.

14. The process of claim 1, wherein the vapor feeds are introduced into the reaction zone with a velocity of at least about 100 feet per second.

15. The process of claim 14, wherein the vapor feeds are introduced into the reaction zone with a velocity of between about 200 and about 250 feet per second.

16. The process of claim 1, wherein a high degree of turbulence in said mixing nozzle is provided by preheating the reactants.

17. The process of claim 2, wherein said hydrocarbon feedstock is propane, said chlorine is introduced in an amount sufficient to leave between about 5.0 and about 7.0 volume percent of free chlorine in the resulting product mixture, the ratio by weight of carbon tetrachloride to hydrocarbon feedstock introduced into said mixing zone is between about 20 and 25, the reaction temperature is between 575° and 625° C., and the pressure in the reaction zone is between about 0 and about 3.5 atmospheres.

18. A process for making perchloroethylene by thermal noncatalytic chlorination of ethylene dichloride under conditions which maximize consumption of carbon tetrachloride, which process comprises: introducing the following materials into a mixing zone:
(a) ethylene dichloride and chlorine, said chlorine being introduced in an amount sufficient to convert the ethylene dichloride to perchloroethylene and result in free chlorine in the product mixture; and
(b) carbon tetrachloride as a reactive diluent, said carbon tetrachloride introduced being between about 50% and about 85% by weight vapor and between about 50% and about 15% by weight liquid and wherein the amount of carbon tetrachloride so introduced is sufficient to maintain the temperature in the range of between about 500° and about 700° C.;

discharging the resulting mixture from said mixing zone into a reaction zone wherein the temperature is maintained within said temperature range and wherein carbon tetrachloride is consumed and perchlaroethylene is produced;

withdrawing a product mixture from the reaction zone;

condensing said mixture; and separating a perchloroethylene fraction and a carbon tetrachloride fraction therefrom.

19. The process of claim 18, wherein said chlorine is introduced in an amount sufficient to leave between about 5 and about 9 volume percent of free chlorine in the resulting product mixture.

20. The process of claim 19, wherein the ratio by weight of carbon tetrachloride to hydrocarbon feedstock introduced into said mixing zone is between 1.5 and 2.5.

21. The process of claim 1, wherein the hydrocarbon feedstock is selected from the group consisting of methane, ethane, propane, ethylene, propylene, chloroform, methyl chloride, ethyl chloride, ethylene dichloride, trichloroethane and trichloropropane.

* * * * *